US010709620B2

(12) United States Patent
Arai et al.

(10) Patent No.: US 10,709,620 B2
(45) Date of Patent: Jul. 14, 2020

(54) TOUCH FASTENER FEMALE MATERIAL, TOUCH FASTENER, AND ABSORBENT ARTICLE

(71) Applicant: 3M INNOVATIVE PROPERTIES COMPANY, St. Paul, MN (US)

(72) Inventors: Nobuharu Arai, Kanagawa (JP); Yasuhiro Kono, Kanagawa (JP)

(73) Assignee: 3M Innovative Properties Company, St. Paul, MN (US)

( * ) Notice: Subject to any disclaimer, the term of this patent is extended or adjusted under 35 U.S.C. 154(b) by 443 days.

(21) Appl. No.: 15/523,236

(22) PCT Filed: Nov. 4, 2015

(86) PCT No.: PCT/US2015/058953
§ 371 (c)(1),
(2) Date: Apr. 28, 2017

(87) PCT Pub. No.: WO2016/073554
PCT Pub. Date: May 12, 2016

(65) Prior Publication Data
US 2017/0319407 A1    Nov. 9, 2017

(30) Foreign Application Priority Data
Nov. 4, 2014    (JP) ................................. 2014-224500

(51) Int. Cl.
*A61F 13/62*    (2006.01)
*D04B 21/02*    (2006.01)
(Continued)

(52) U.S. Cl.
CPC .......... *A61F 13/62* (2013.01); *A44B 18/0034* (2013.01); *D04B 21/02* (2013.01);
(Continued)

(58) Field of Classification Search
CPC ............. A44B 18/0023; A44B 18/0034; A61F 13/62–627; D10B 2501/0632; D04B 1/02
See application file for complete search history.

(56) References Cited

U.S. PATENT DOCUMENTS 4,315,419 A  *  2/1982  Kernbichler ........... D04B 21/02
                                                            66/194
4,677,011 A  *  6/1987  Matsuda ............ A44B 18/0034
                                                            428/100
(Continued)

FOREIGN PATENT DOCUMENTS

DE        2511505       9/1976
EP        1350879       10/2003
(Continued)

OTHER PUBLICATIONS

International Search Report for PCT International Application No. PCT/US2015/058953, dated Feb. 9, 2016, 5 pages.

*Primary Examiner* — Susan S Su

(57) ABSTRACT

Problem: To provide a touch fastener female material which can achieve a good printed appearance without using a substrate layer such as a printed layer support film and which has excellent engaging properties and durability, and a touch fastener and absorbent article containing the touch fastener female material. Solution: A touch fastener female material including a knitted fabric; the knitted fabric composed of back yarns, middle yarns, and front yarns; at least 50% of the back yarns being finished yarns; and the back yarns being arranged in accordance with a 0-0/N-N (where N is an odd number) knit structure.

7 Claims, 7 Drawing Sheets

(51) Int. Cl.
 *D04B 21/18* (2006.01)
 *A44B 18/00* (2006.01)
 *D04B 21/20* (2006.01)

(52) U.S. Cl.
 CPC .............. *D04B 21/18* (2013.01); *D04B 21/20* (2013.01); *D10B 2501/0632* (2013.01)

(56) References Cited

U.S. PATENT DOCUMENTS

| | | | | |
|---|---|---|---|---|
| 4,709,562 | A | * | 12/1987 | Matsuda ............ A44B 18/0034 24/445 |
| 4,838,044 | A | * | 6/1989 | Matsuda ............ A44B 18/0034 66/190 |
| 5,373,712 | A | * | 12/1994 | Yamamoto ......... A44B 18/0034 66/195 |
| 5,422,153 | A | * | 6/1995 | Miyamoto ............. D04B 21/02 428/116 |
| 5,429,555 | A | * | 7/1995 | Beckh ................. B29C 70/226 112/63 |
| 5,699,593 | A | | 12/1997 | Jackson |
| 6,096,667 | A | | 8/2000 | Rhode |
| 6,099,932 | A | | 8/2000 | Gehring |
| 6,196,031 | B1 | * | 3/2001 | Ducauchuis ....... A44B 18/0034 24/445 |
| 6,216,496 | B1 | | 4/2001 | Gehring |
| 6,845,639 | B1 | * | 1/2005 | Hajek ................ A44B 18/0034 66/195 |
| 2002/0006758 | A1 | * | 1/2002 | Desgrand ............... D04B 21/02 442/312 |
| 2004/0219854 | A1 | * | 11/2004 | Groitzsch ........... A61F 13/4902 442/328 |
| 2005/0003143 | A1 | * | 1/2005 | Ducauchuis ....... A44B 18/0011 428/92 |
| 2005/0208260 | A1 | * | 9/2005 | Baldauf ............. A44B 18/0069 428/95 |
| 2006/0080810 | A1 | * | 4/2006 | Horn .................. A44B 18/0073 24/445 |
| 2006/0182927 | A1 | * | 8/2006 | Baldauf ................. D04B 21/02 428/99 |
| 2008/0009819 | A1 | * | 1/2008 | Liu .................... A44B 18/0034 604/385.23 |
| 2012/0010588 | A1 | * | 1/2012 | Morishita .......... A44B 18/0034 604/391 |
| 2012/0231206 | A1 | | 9/2012 | Thompson, Jr. |
| 2016/0185071 | A1 | * | 6/2016 | Homoelle ............... B32B 5/026 428/92 |

FOREIGN PATENT DOCUMENTS

| | | | |
|---|---|---|---|
| JP | 61119756 A | * 6/1986 | ............. D04B 21/18 |
| JP | 06-280171 | 10/1994 | |
| JP | 2004-236960 | 8/2004 | |
| JP | 2005-253667 | 9/2005 | |
| JP | 2006-081720 | 3/2006 | |
| JP | 2008-088602 | 4/2008 | |
| JP | 2010/063585 | 3/2010 | |
| JP | 2010-063633 | 3/2010 | |
| JP | 2010-253183 | 11/2010 | |
| JP | 2012-034802 | 2/2012 | |
| WO | WO 1999-44457 | 9/1999 | |
| WO | WO 2004-050970 | 6/2004 | |

* cited by examiner

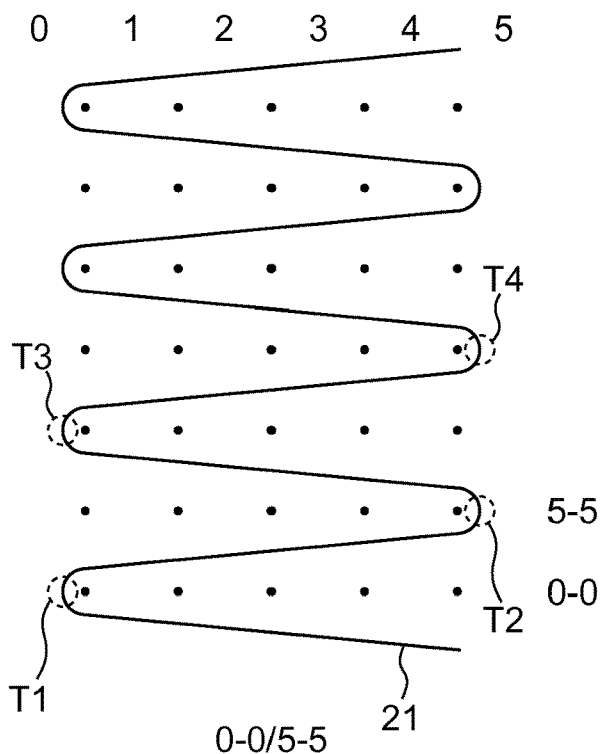
Fig. 3B-a
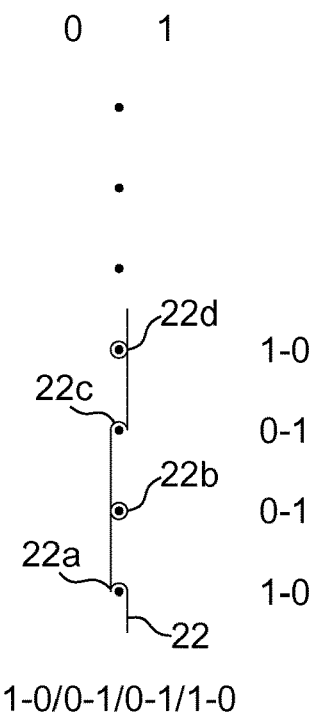
Fig. 3B-b
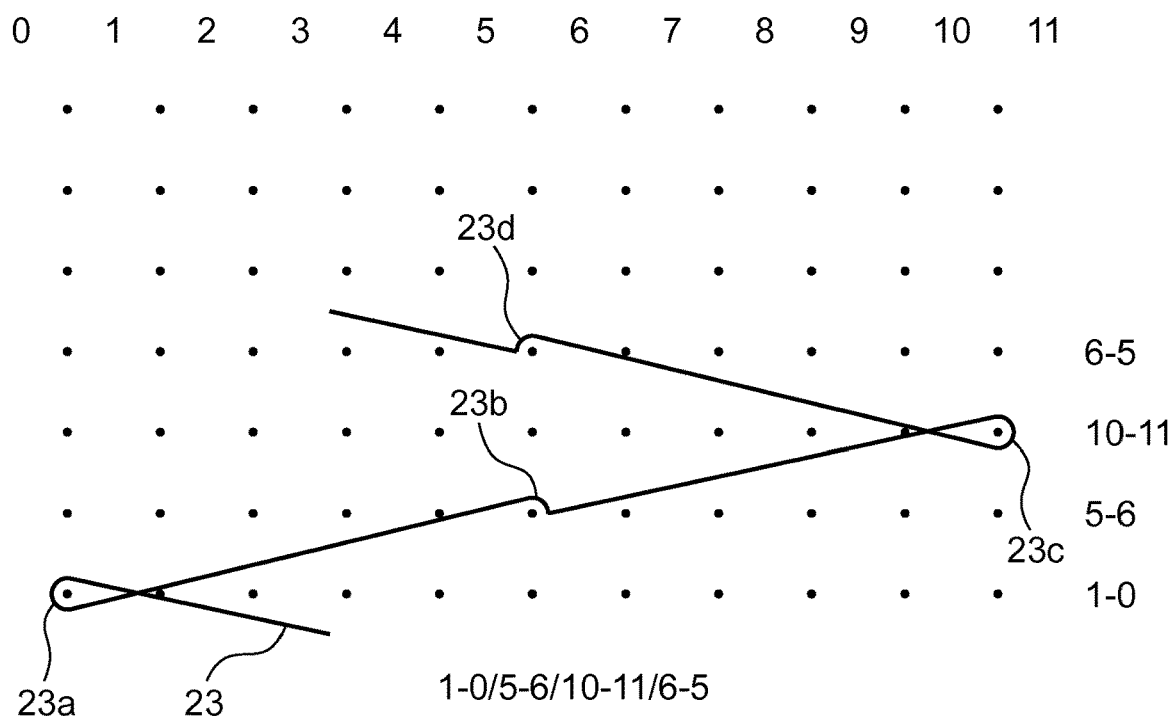
Fig. 3B-c

TOUCH FASTENER FEMALE MATERIAL, TOUCH FASTENER, AND ABSORBENT ARTICLE

CROSS REFERENCE TO RELATED APPLICATIONS

This application is a national stage filing under 35 U.S.C. 371 of PCT/US2015/058953, filed Nov. 4, 2015, which claims the benefit of JP Application No. 2014-224500, filed Nov. 4, 2014, the disclosure of which is incorporated by reference in its/their entirety herein.

TECHNICAL FIELD

The present disclosure relates to a touch fastener female material, a touch fastener, and an absorbent article.

BACKGROUND TECHNOLOGY

Touch fasteners have conventionally been widely used to fasten and unite various articles such as textile products, plastic products, paper products, industrial parts, electronic parts, and construction materials. For example, there are known absorbent articles (for example, disposable diapers and the like) to which touch fasteners are attached as engaging materials. Touch fasteners of various engaging formats are known, such as, for example, a touch fastener consisting of a pair of a male material having a hook-shaped engaging element and a female material having a loop-shaped engaging material.

Patent Document 1 describes a weft-inserted warp-knit fabric which is used as a female knitted fabric with a fastener consisting of a hook and a loop, the fabric having a front side and a back side. The back side thereof has a plurality of stitch wheels distanced from one another, wherein the loop part of the stitches projects outward and is connected to the wheel at only the base, and the loops adjacent to each wheel include a weft-inserted warp-knitted fabric forming a free loop which is alternately inclined in the horizontal direction in an appropriate direction, and a weft which is inserted into the side of the knitted fabric between the front and back sides thereof and extends so as to traverse the entire width of the knitted fabric.

Patent Document 2 describes a loop material containing a continuous multifilament textured yarn linked intermittently to a substrate, wherein the yarn is less than 50 denier, and has a fracture energy of at least 60 Joules/g, and stretch of less than 45%.

Patent Document 3 describes a warp-knitted fabric for use as a loop member of a hook and loop touch fastening system, the fabric including a base structure formed from a base yarn and a pile structure formed from a pile yarn. The pile yarn is a strong monofilament yarn of at least 7 grams/denier and approximately 50 to 200 denier and has a height of from 2.0 to 3.0 millimeters, and the respective pile yarns define loops fixed to the base structure and are directed at various angles relative to one another.

Patent Document 4 describes a loop part for a hook-and-loop fastener, wherein the loop part includes a warp-knitted base formed from a plurality of interconnected yarns, and a plurality of continuous long floats extending away from the warp-knitted base and linked thereto. The long floats are formed from a monofilament pile yarn, and the floats are formed into loops for the hook-and-loop fastener. The loops are arranged into coextensive loop yarns and extend in the same direction.

PRIOR ART DOCUMENTS

Patent Documents

Patent Document 1: U.S. Pat. No. 6,096,667, Specification
Patent Document 2: U.S. Patent Application Publication No. 2012/0231206, Specification
Patent Document 3: U.S. Pat. No. 6,216,496, Specification
Patent Document 4: U.S. Pat. No. 6,099,932, Specification

SUMMARY OF THE INVENTION

Problem to be Solved by the Invention

When a touch fastener including a pair of a female material and a male material is used as an engaging member in an absorbent article such as a diaper, numbers, ruled lines, or the like are preferably printed on the female material as a reference for the engaging position of the male material. For example, by forming a printed layer on the non-engaging surface side of a base material (for example, a knitted fabric, a nonwoven fabric, or the like), in which one of the two main surfaces is an engaging surface and the other is a non-engaging surface, it is possible to obtain a touch fastener female material having a printed layer. In this case, the base material has a degree of optical transparency so that the printed layer can be visually confirmed through the base material. As a result, it is possible to form a touch fastener female material with a design. Conventionally, as a method for manufacturing a touch fastener having a printed layer, a method of disposing a printed film, which has a printed layer support film and a printed layer disposed thereon, on the base material has been used. However, examples of films that can be used as a printed layer support film include a CPP (cast polypropylene) film and a BOPP (biaxially oriented polypropylene) film, and the like, but these films are ordinarily air-impermeable, which may cause a decrease in the air permeability, flexibility, and extensibility of an article to which the touch fastener female material is attached and may diminish the comfort or fit when an absorbent article such as a diaper is worn. Accordingly, it was necessary to take measures such as securing an air-permeable portion and an extensible portion by forming the touch fastener female material into several strip shapes. In addition, the raw material cost of the printed layer support film and the production cost of the adhesive for adhering the base material and the printed film cannot be ignored. Therefore, there is a demand for a touch fastener female material with which issues such as those described above can be avoided while having a design.

Knitted fabrics conventionally used as materials suitable for obtaining a base material having sufficient air permeability and engaging properties do not have a non-engaging surface of a form suitable for printing. That is, even if printing is performed directly on the non-engaging surface (that is, without printing through a substrate layer such as a printed layer support film), it was not possible to achieve a good printed appearance. On the other hand, although a touch fastener female material configured of a nonwoven fabric has excellent air permeability and printing suitability, it may not be possible to achieve sufficient engaging properties and durability in comparison to a touch fastener female material made from a knitted fabric.

An object of the present invention is to solve the problems described above and to provide a touch fastener female material which can achieve a good printed appearance without using a substrate layer such as a printed layer support film and has excellent engaging properties and durability, and a touch fastener and absorbent article containing the touch fastener female material.

Means for Solving the Problems

The present invention has the following configuration.

[1] A touch fastener female material including a knitted fabric;

the knitted fabric obtained by knitting back yarns, middle yarns, and front yarns;

at least 50% of the back yarns being finished yarns; and the back yarns being arranged in accordance with a 0-0/N-N (where N is an odd number) knit structure.

[2] A touch fastener including the touch fastener female material and a touch fastener male material.

[3] An absorbent article including the touch fastener female material.

Effect of the Invention

According to the present invention, a touch fastener female material including a knitted fabric having a non-engaging surface with excellent smoothness and concealment is provided. The touch fastener female material thereof can achieve a good printed appearance without using a substrate layer such as a printed layer support film and has excellent engaging properties and durability.

BRIEF DESCRIPTION OF THE DRAWINGS

FIG. 3B is a schematic diagram illustrating the knit structure of the knitted fabric illustrated in FIG. 3A in exploded views of the back yarn, the middle yarn, and the front yarn, wherein (a) illustrates the knit structure of the back yarn, (b) illustrates the knit structure of the middle yarn, and (c) illustrates the knit structure of the front yarn.

MODES FOR CARRYING OUT THE INVENTION

Exemplary embodiments of the present invention will be described hereinafter, but the present invention is not limited to the embodiments below, and it is intended that any modifications that do not depart from the spirit and scope of the Scope of the Patent Claims be included in the present invention. In addition, it is to be understood that unless specified otherwise, the various measurements mentioned in the present disclosure are performed with the methods described in the "Examples" or methods understood to be equivalent thereto by persons skilled in the art.

One embodiment of the present disclosure provides:

a touch fastener female material including a knitted fabric;

the knitted fabric being obtained by knitting back yarns, middle yarns, and front yarns;

at least 50% of the back yarns being finished yarns; and the back yarns being arranged in accordance with a 0-0/N-N (where N is an odd number) knit structure.

In the touch fastener female material of the present disclosure (also simply called the "female material" in the present disclosure), one of the two main surfaces may be an engaging surface (that is, a surface meant to be engaged with a male material), and the other may be a non-engaging surface (that is, a surface not meant to be engaged with a male member). The engaging surface is provided with an engaging element. This engaging element includes a loop engaging element formed by a loop-shaped yarn. Accordingly, the engaging surface of the touch fastener female material can engage with the engaging element (for example, a hook engaging element) of the male material. Thus, in a typical embodiment, the engaging format of the touch fastener is a hook-and-loop format. A hook-and-loop type touch fastener may be a pair of a male materials having a hook configured by a protrusion projecting in the thickness direction of the touch fastener and a female material having a loop capable of engaging with the hook.

Figure 1:
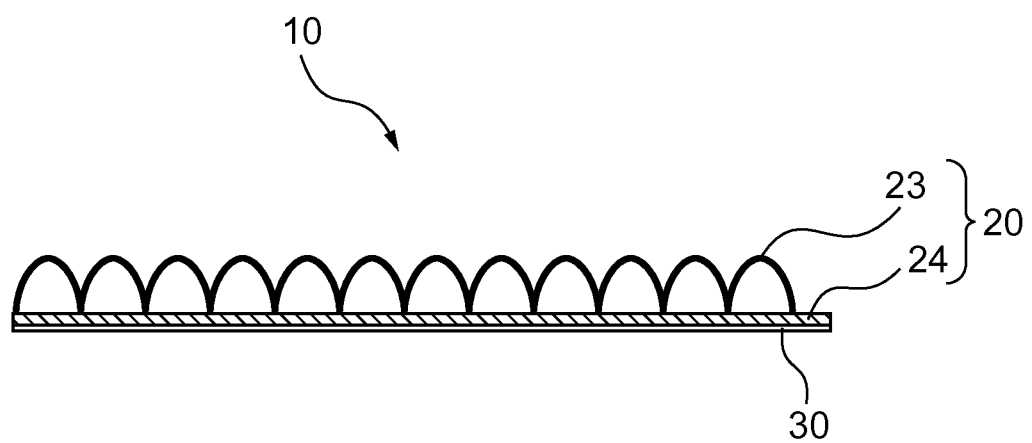
FIG. 1 is a schematic diagram illustrating the cross-sectional structure of the touch fastener female material of one embodiment of the present disclosure.
Figure 2A:
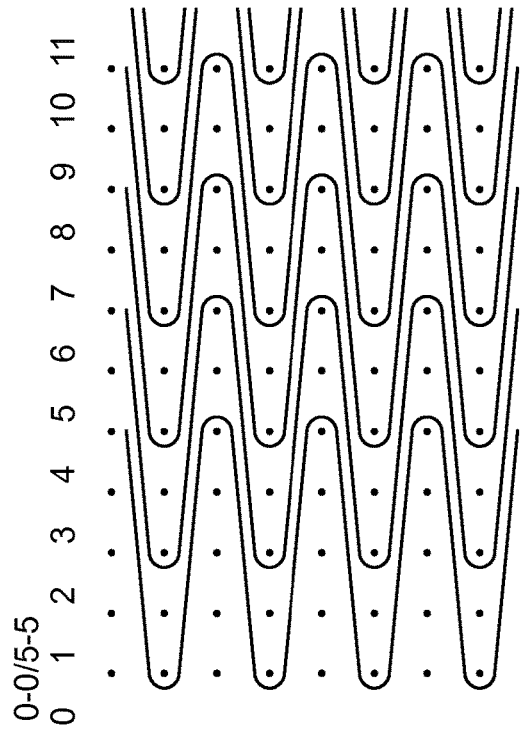
FIG. 2 is a schematic diagram illustrating the knit structure of the back yarn in the touch fastener female material of one embodiment of the present disclosure, wherein (a) represents a 0-0/3-3 knit structure, (b) represents a 0-0/5-5 knit structure, (c) represents a 0-0/7-7 knit structure, and (d) represents a 0-0/9-9 knit structure.
Figure 2B:
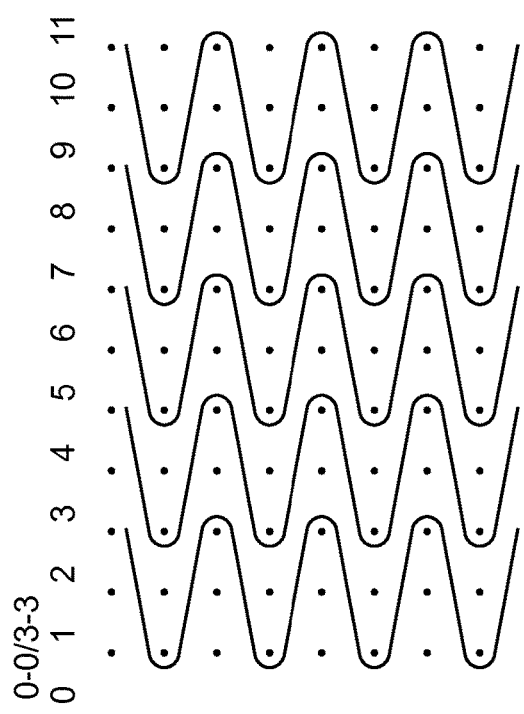
Figure 2C:
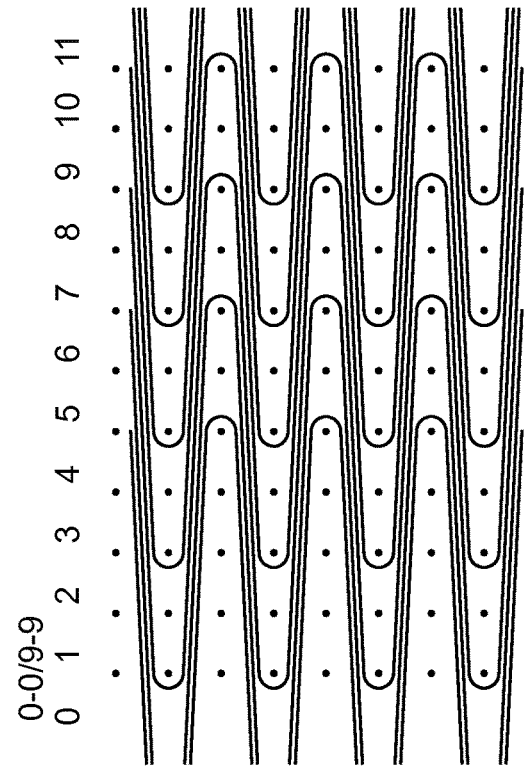
Figure 2D:
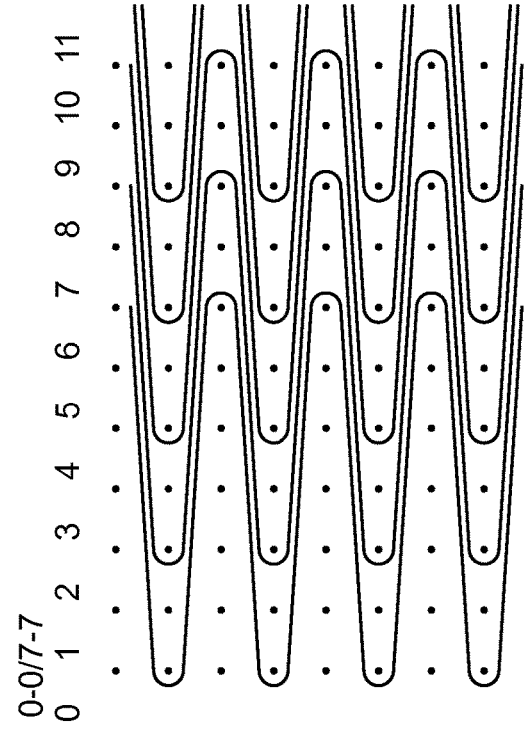

FIG. 1 is a schematic diagram illustrating the cross-sectional structure of the touch fastener female material of one embodiment of the present disclosure. Referring to FIG. 1, a touch fastener female material 10 of the present disclosure includes a knitted fabric 20. The knitted fabric has good air permeability, flexibility, and extensibility in the width direction due to a structure in which yarns are knitted together. These characteristics are particularly advantageous when using the female material in an absorbent article such as a sanitary product. In addition, in several embodiments, the durability may be better than that of a nonwoven fabric, for example, due to the structure in which the yarns are knitted together. The knitted fabric 20 includes a loop structure configured of a base structure 24 and a front yarn 23 on the base structure 24. In a typical embodiment, the touch fastener female material 10 may further include a printed part 30 on the knitted fabric 20.

The knitted fabric in the present disclosure is knitted with a back yarn, a middle yarn, and a front yarn. Such a knitted fabric can be knitted with a typical knitting machine (for example, a three-bar knitting machine, or, for example, a four-bar knitting machine in the embodiment described below when elastic yarn is used, or the like) equipped with a back bar, a middle bar, and a front bar. Accordingly, the knitted fabric of the present disclosure can be produced simply and at low cost. In a typical embodiment, the back yarn, middle yarn, and front yarn are respectively threaded over the back bar, the middle bar, and the front bar. The threading format may be through threading, one-in-one-out (that is, every other yarn is drawn out), one-in-two-out (that is, one yarn threaded and two yarns drawn out), or the like. The one-in-one-out format is advantageous from the perspectives of air permeability, flexibility, and extensibility and for forming the structure of the female material of the present invention.

The back yarn and the middle yarn together constitute the base structure 24 of the knitted fabric 20 and contribute to the mounting of the female material on the application part (for example, the cloth of an absorbent article) of the target article (for example, an absorbent article). The front yarn 23 is primarily exposed to a first surface side of the knitted fabric so as to form a loop engaging element. Accordingly, this first surface of the knitted fabric can function as an engaging surface of the female material (that is, a surface to be engaged with a male material). The back yarn is primarily exposed to a second surface side opposite the first surface side of the knitted fabric. The second surface is a non-engaging surface of the female material. The non-engaging surface can function as a mounting surface when the female material is mounted on the target article.

In a typical embodiment of the present disclosure, the female material further has a printed part. As illustrated in FIG. 1, a printed part 30 is disposed directly on the non-engaging surface of the base structure 24 of the knitted fabric 20. That is, the printed part 30 can be provided on the non-engaging surface of the base structure 24 of the knitted fabric 20. In addition, a part of the printed part 30 may be present between each of the yarns (back yarn and middle yarn) constituting the base structure 24 of the knitted fabric 20. In the present disclosure, the non-engaging surface is meant to have smoothness and concealment suitable for printing (in particular, printing through coating). The female material of the present disclosure has good air permeability, flexibility, and extensibility due to the contribution of the knitted fabric while also contributing to the good smoothness and concealment of the non-engaging surface, which yields the advantage that the printed part can be disposed on the knitted fabric without using a substrate layer (for example, a printed layer support film or the like). That is, while a substrate layer may cause a loss in the air permeability, flexibility, and extensibility of the female material, the printed part can be disposed directly on the knitted fabric of the female material of the present disclosure since the material does not have such a substrate layer. As a result, it is possible to provide a female material having air permeability, flexibility, and extensibility while having a printed part. Moreover, in the present disclosure, the smoothness of the non-engaging layer is influenced by the difference between the knitted fabric thickness at the stitch parts (junction parts) and the knitted fabric thickness between stitches (the areas between two adjacent middle yarns). The surface is smoother when this difference in thickness is smaller. In addition, the concealment can be assessed by comprehensively evaluating the Lab color space (L*) and the external appearance of the non-engaging surface. The concealment becomes higher as the light transmittance becomes smaller or as the Lab color space (L*) value becomes larger. The external appearance of the non-engaging surface can be confirmed by a visual observation of the external appearance.

The fact that the non-engaging surface has good smoothness and concealment further provides the following advantages when the touch fastener female material of the present disclosure is used in an absorbent article (for example, a diaper) application. In the assembly line of an absorbent article, conveyance by a suction hole provided in a suction roll is necessary in order to attach the touch fastener to the main body of the absorbent article. At this time, if there are too many gaps in the touch fastener, or if the unevenness in the surface on the side of the touch fastener opposite the suction roll is too large, the conveyance of the touch fastener female material with the suction roll becomes difficult, and this may cause the problem of reduced productivity. The touch fastener female material of the present disclosure avoids such problems, and thereby provides the advantage of contributing to good productivity in the production line of an absorbent article (for example, a diaper).

The present inventors discovered the importance of the smoothness and concealment of the non-engaging surface when performing printing on the non-engaging surface of the touch fastener female material and further focused attention on the fact that the smoothness and concealment described above can be controlled by selecting the back yarn and controlling the knit structure.

In the present disclosure, the back yarn is arranged in accordance with a 0-0/N-N (where N is an odd number) knit structure. That is, since the back yarn is arranged as an inserted structure, the overlapping of yarn in the knitted fabric thickness direction can be reduced in comparison to cases having stitches (in particular, seams), and the yarn can be distributed widely in the plane direction of the knitted fabric. Accordingly, such a back yarn contributes to the good smoothness of the non-engaging surface and the good concealment of the knitted fabric.

In addition, the back yarn includes a finished yarn. Due to the yarn arrangement resulting from the 0-0/N-N knit structure, the processing (twisting or the like) of finished yarn becomes relatively easy to undo, and single yarns are easily dispersed. In this respect as well, the arrangement of the back yarn of the present disclosure is also advantageous from the perspective of obtaining a knitted fabric surface having excellent smoothness and concealment.

In the present disclosure, N of the knit structure described above is an odd number. The format of yarn feeding to the bars can be selected in accordance with the intended purpose such as the basis weight of the knitted fabric, but with the 0-0/N-N knit structure, the one-in-one-out threading format can be employed favorably.

FIG. 2 is a schematic diagram illustrating the knit structure of the back yarn in the touch fastener female material of one embodiment of the present disclosure, wherein (a) represents a 0-0/3-3 knit structure, (b) represents a 0-0/5-5 knit structure, (c) represents a 0-0/7-7 knit structure, and (d) represents a 0-0/9-9 knit structure. That is, FIG. 2 illustrates an organizational chart of cases in which N is 3 (FIG. 2(a)), N is 5 (FIG. 2(b)), N is 7 (FIG. 2(c)), and N is 9 (FIG. 2(d)). In a preferred embodiment, N is 5, 7, or 9 from the perspective of obtaining a knitted fabric with good air permeability, flexibility, and extensibility as well as good smoothness and concealment. In certain embodiments, N is more preferably 5 or 7.

Figure 3A:
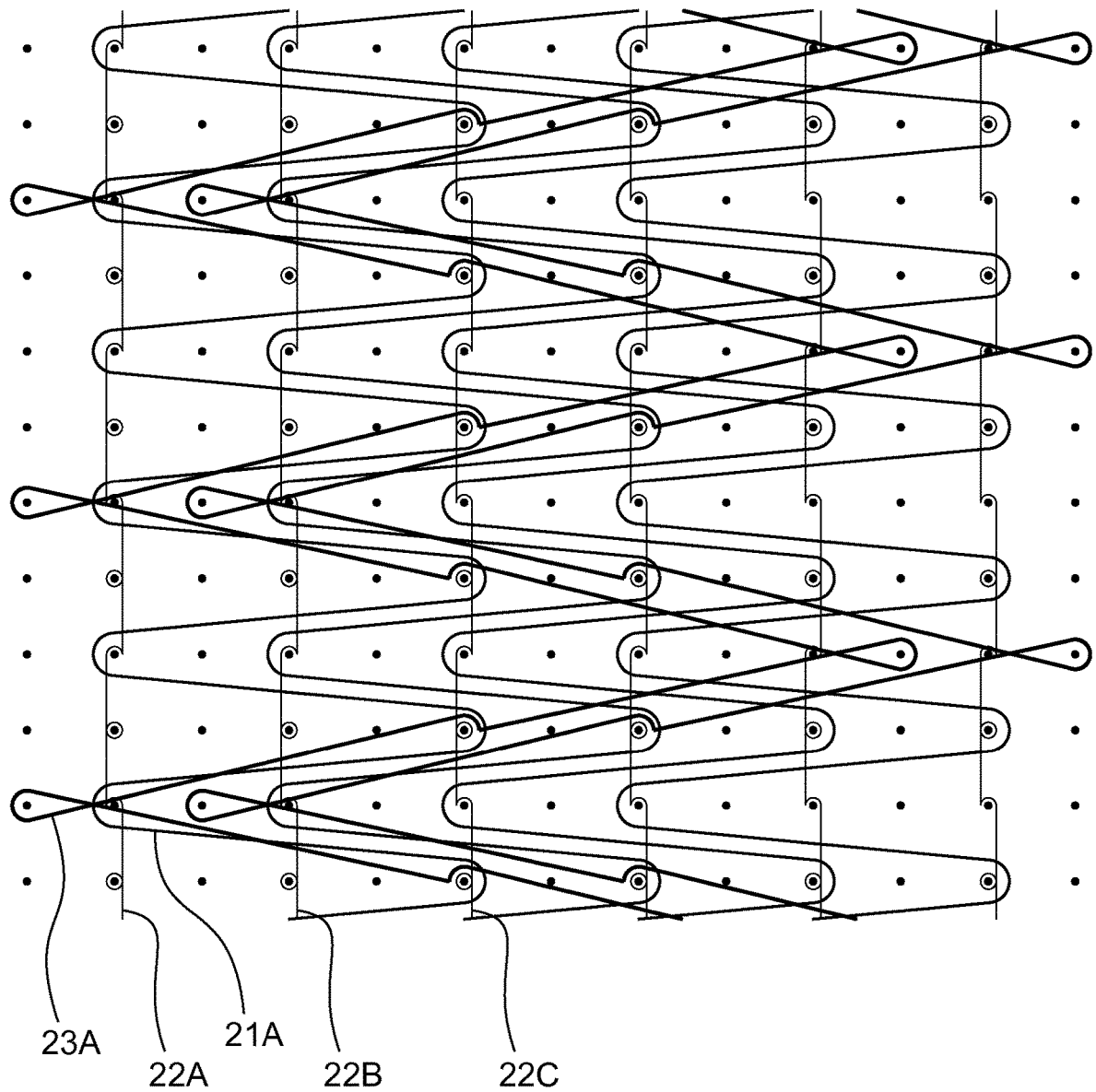
FIG. 3A is a schematic diagram illustrating the knit structure of the knitted fabric in the touch fastener female material of one embodiment of the present disclosure.

FIG. 3A is a schematic diagram illustrating the knit structure of the knitted fabric in the touch fastener female material of one embodiment of the present disclosure. FIG. 3B is a schematic diagram illustrating the knit structure of the knitted fabric illustrated in FIG. 3A in exploded views of the back yarn, the middle yarn, and the front yarn, wherein (a) illustrates the knit structure of the back yarn, (b) illustrates the knit structure of the middle yarn, and (c) illustrates the knit structure of the front yarn. FIGS. 3A and 3B illustrate that the back yarns 21 and 21A are arranged with the knit structure 0-0/5,5, the middle yarns 22, 22A, 22B, and 22C are arranged with the knit structure 1-0/0-1/0-1/1-0, and the front yarns 23 and 23A are arranged with the knit structure 1-0/5-6/10-11/6-5.

The back yarns 21 and 21A are inserted into the chain stitches of the middle yarns 22, 22A, 22B, and 22C with a 0-0/N-N (for example, 0-0/5-5 in FIGS. 3A and 3B) knit structure.

In a preferred embodiment, the seams and laps of the middle yarns are formed alternately (preferably, alternately for each course), and the back yarns are respectively connected alternately to two middle yarns at each end part on the 0-0 side and the N-N side. Here, the back yarns are connected to the seam of one of the two middle yarns at one end part on the 0-0 side or the N-N side and to the lap of the other of the two middle yarns at the other end part on the 0-0 side or the N-N side. Such a knit structure contributes to a good engaging force of the female material with respect to the male material in addition to good smoothness and concealment. A touch fastener with a large engaging force is advantageous for the prevention of leakage in an absorbent article such as a sanitary product, for example. In the present disclosure, each end part on the 0-0 side and the N-N side of the back yarn refers to the position of the back yarn at each end part in the well direction—that is, the position on each vertex side of the back yarn indicated by the waveform.

One example of such an embodiment is the knit structure illustrated in FIGS. 3A and 3B. In this knit structure, the back yarns, middle yarns, and front yarns are respectively threaded for every other well (that is, one-in-one-out). In FIG. 3B, one of each of the back yarn, middle yarn, and front yarn are illustrated in order to explain the pattern of the knit structure of the back yarns, middle yarns, and front yarns. The laps and seams of the middle yarns 22, 22A, 22B, and 22C are formed alternately for each course. Referring to FIG. 3B, the middle yarn 22 has an alternating arrangement consisting of a lap 22a of the first course, a seam 22b of the second course, a lap 22c of the third course, and a seam 22d of the fourth course. The back yarns arranged in accordance with the 0-0/N-N knit structure are alternately connected to two middle yarns for each course (specifically, the seam of one middle yarn and the lap of the other middle yarn) at the well direction end parts (in FIG. 3B, these are illustrated as the end parts T1, T2, T3, and T4 for the first through fourth courses). That is, referring to FIG. 3A, when focusing attention on a given back yarn 21A, this back yarn 21A is connected to the lap of the middle yarn 22A (corresponding to the lap 22a in FIG. 3B(b)) at the end part in the first course (corresponding to the end part T1 in FIG. 3B(a)), the seam of the middle yarn 22C (corresponding to the seam 22b in FIG. 3B(b)) at the end part in the second course (corresponding to the end part T2 in FIG. 3B(a)), the lap of the middle yarn 22A (corresponding to the lap 22c in FIG. 3B(b)) at the end part in the third course (corresponding to the end part T3 in FIG. 3B(a)), and the seam of the middle yarn 22C (corresponding to the seam 22d in FIG. 3B(b)) at the end part in the fourth course (corresponding to the end part T4 in FIG. 3B(a)), respectively.

The front yarns are arranged so as to form loops. Examples of the knit structure of the front yarns include, in addition to 1-0/5-6/10-11/6-5 (the embodiment illustrated in FIGS. 3A and 3B), 1-0/3-4/6-7/4-3 (type in which the pitch in the horizontal direction is narrower than in the knit structure described above) and 0-1/5-6/11-10/6-5 (lap type). The loops contribute to the engagement of the female material with the male material.

In a preferred embodiment, the seams and the laps of the middle yarns are formed alternately (preferably, alternately for each course). The front yarns have at least laps arranged at the positions of the seams of the middle yarns, and the front yarns alternately project to the left and right with respect to the middle yarns.

Figure 4A:
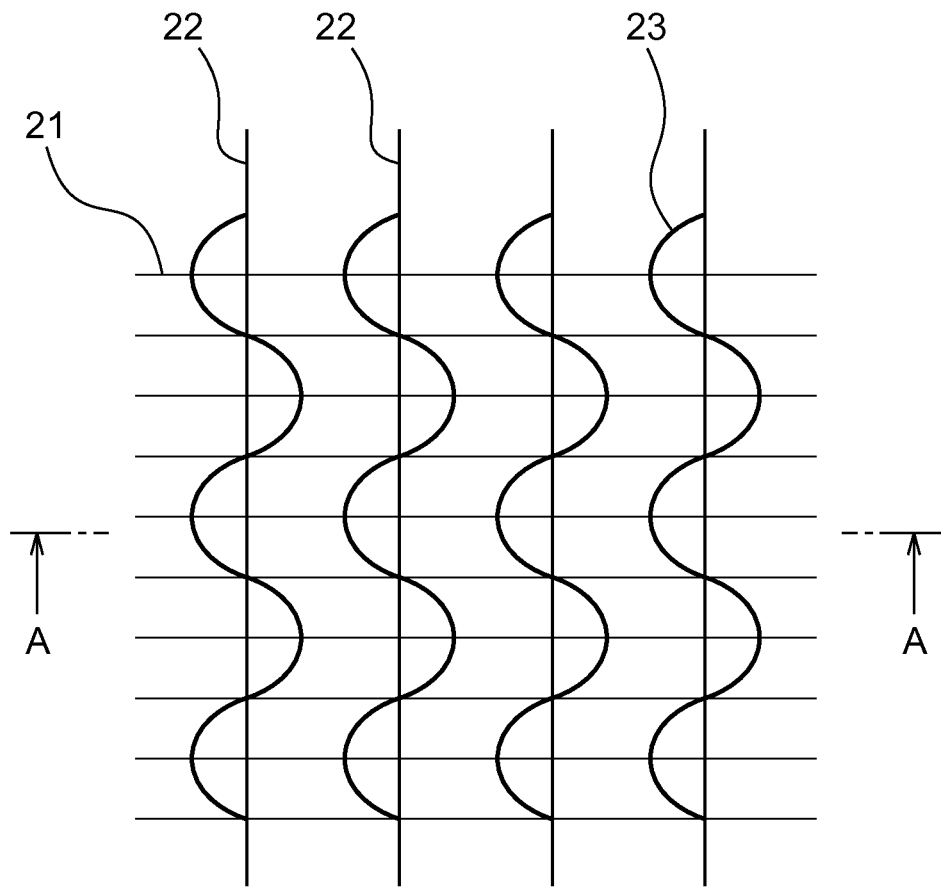
FIG. 4A is a schematic diagram illustrating the knitted fabric according to the knit structure illustrated in FIGS. 3A and 3B.
Figure 4B:
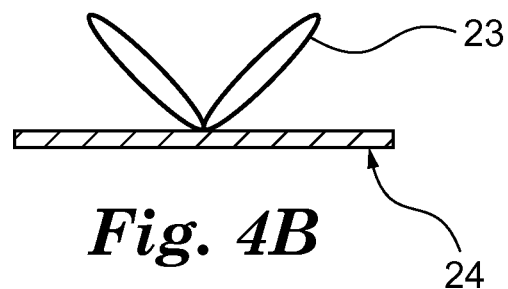
FIG. 4B is a schematic diagram illustrating a state of the front yarn formed in the knitted fabric as observed when the knitted fabric is cut along line A-A in FIG. 4A (in the direction perpendicular to the flow direction of the middle yarn) (one loop each on the left and right).

FIG. 4A is a schematic diagram illustrating the knitted fabric according to the knit structure illustrated in FIGS. 3A and 3B. FIG. 4B is a schematic diagram illustrating a state of the front yarn formed in the knitted fabric as observed when the knitted fabric is cut along line A-A in FIG. 4A (in the direction perpendicular to the flow direction of the middle yarn) (one loop each on the left and right). Referring to FIGS. 3A and 3B and FIGS. 4A and 4B, when focusing attention on a given front yarn 23A, this front yarn 23A is connected to the seams of the middle yarn 22C (corresponding to the seams 22b and 22d of FIG. 3B(b)) at the laps of the second and fourth courses (corresponding to the laps 23b and 23d of FIG. 3B(c)). As a result of this knit structure, as illustrated in FIG. 4B, it is possible to form a structure in which the front yarns alternately project to the left and right with respect to the middle yarns from only one of the surfaces of the knitted fabric. In this case, the seams 23a and 23c of the first and third courses of the front yarn 23 are typically pressed off. As a result, the front yarns are drawn to the left and right with respect to the middle yarns so as to form piles of the knitted fabric.

Referring further to FIGS. 3A and 3B and FIGS. 4A and 4B, more specifically, the front yarn 23 is first lapped (1-0 position of the knit structure) by a seam or lap (a seam in the drawing) from left to right at a prescribed needle position of the knitted fabric 20 and is drawn in the right direction. The front yarn 23 that is drawn to the right is then connected to the seam 22b of the middle yarn 22 in the state of the lap 23b in the second course and is further drawn in the right direction of the knitted fabric 20. Next, it is lapped (10-11 position of the knit structure) by a seam or lap (a seam in the drawing) from right to left at a prescribed needle position of the knitted fabric 20 and drawn in the left direction. The front yarn 23 that is drawn to the left is then connected to the seam 22d of the middle yarn 22 in the state of the lap 23d with the fourth course and is further drawn in the left direction of the knitted fabric 20. This is repeated so that the front yarns 23 alternately project to the left and right with respect to the base structure 24 from only one surface of the knitted fabric so as to form piles, as illustrated in FIG. 4B, for example.

Here, the statement that "the front yarns alternately project to the left and right with respect to the middle yarn from only one surface of the knitted fabric" means when a cross section of the knitted fabric 20 is viewed in the direction perpendicular to the direction of the middle yarns 22, the front yarns 23 are formed alternately in the left and right directions while maintaining a constant range of angles around the junctions with the middle yarn parts with respect to the surface of the base structure 24. Accordingly, the front yarns are meant to be formed to the left and right of the middle yarns, and the front yarns are meant to be easily engaged with the engaging elements of the male material. When the front yarns alternately project to the left and right with respect to the middle yarns from one surface of the knitted fabric, the difference between the engaging force on the left and right is preferably small (the difference in the force perceived when the male material is peeled is small).

The pattern of the knit structure of the back yarn, the middle yarn, and the front yarn may respectively be one type for the entire knitted fabric, or a plurality of types may be mixed. A knitted structure made from one type or a plurality of types of patterns can be designed appropriately by a person skilled in the art with the knitted fabric by the threading method of the knitting machine and the control of the knitting program.

The middle yarn and front yarn may each be a single filament or a bundle of a plurality of filaments (that is, multifilaments). In a preferred embodiment, the middle yarn is a monofilament from the perspective of smoothness. It is sometimes preferable to use a multifilament front yarn rather than a monofilament front yarn in that it increases the probability of engagement with the male material. In this case, if the filaments of the front yarn are excessively fine, they may be severed during engagement with the male material, so filaments of a moderate thickness are selected based on the shape or the like of the touch fastener. On the other hand, as described above, the back yarn includes a finished yarn, so this is intended to be a multifilament in certain embodiments.

In general, the total fineness of the filaments of the back yarn, middle yarn, and front yarn may be respectively set to approximately 20 to approximately 220 dtex or approximately 20 to approximately 100 dtex. The fineness of a monofilament may be approximately 0.5 to approximately 7 dtex.

The materials of the back yarn, middle yarn, and front yarn may respectively be one type or two or more types of materials and can be designed in accordance with the desired properties of the knitted fabric. In addition, the types of fibers respectively constituting the back yarn, middle yarn, and front yarn may also be one type or two or more types of fibers.

Examples of materials of the middle yarn and the front yarn respectively include polyolefins (for example, polyethylene, polypropylene, and the like), polyesters, polyamides, polyurethanes, EVA (ethylene-vinyl acetate), polylactic acids, rayon, copolymers and mixtures thereof, and natural fibers. In several embodiments, polyamides, which have high strength, are used from the perspective of preventing the breakdown of the female material due to engagement with the male material. In addition, polyesters are preferable when taking into consideration the material cost or environmental stability.

Examples of the material of the back yarn include polyolefins (for example, polyethylene, polypropylene, and the like), polyesters, polyamides, polyurethanes, EVA (ethylene-vinyl acetate), polylactic acids, and copolymers and mixtures thereof. In several embodiments, polyamides, which have high strength, are used from the perspective of preventing the breakdown of the female material due to engagement with the male material. In a preferred embodiment, the back yarn is a polyester from perspectives such as the affinity with ink, strength, material cost, and environmental stability.

At least approximately 50% of the back yarns are finished yarns. In the present disclosure, "at least approximately 50% of the back yarns" refers to at least approximately 50% of the total number of back yarns (that is, the number of back yarns arranged in the well direction in the knitted fabric). The fact that at least approximately 50% of the back yarns are finished yarns is advantageous from the perspective of good smoothness and concealment. In a preferred embodiment, the lower limit of finished yarns in the back yarns is at least approximately 55%, at least approximately 60%, or at least approximately 67%, and the upper limit thereof is at most approximately 100%, at most approximately 90%, or at most approximately 80%. In addition, when the back yarn further includes an elastic yarn or the like described below in addition to a finished yarn, approximately 50% to approximately 80% may be finished yarn out of a total of 100% of finished yarn and elastic yarn from the perspective of obtaining good merits thereof. Further, when elastic yarn is inserted into the back yarn, the elastic yarn may be inserted with a bar differing from that of the finished yarn. That is, in addition to a method of winding elastic yarn and finished yarn around the same beam, elastic yarn may also be inserted into the back yarn with a beam (four bars) differing from that of the finished yarn.

In the present disclosure, finished yarn includes all types of yarn that has undergone processing to impart bulkiness and/or elasticity (for example, crimpability). In a typical embodiment, a yarn provided with bulkiness, crimpability, or the like may be prepared by thermosetting synthetic fibers (by applying dry heat or steam) while twisting the fibers. Finished yarn can be produced, for example, by a twisting/untwisting method, a false twisting method, or the like. In particular, false twisted yarn (for example, one-heater false twisted yarn), which is also called textured yarn, tends to expand favorably so as to fill the gaps of stitches in the knitted fabric, which is advantageous from the perspective of further enhancing the smoothness and concealment. The lower limit of the number of twists in the finished yarn is preferably at least approximately 2,000 tpm (twist per meter) or at least approximately 2,500 tpm, and the upper limit is preferably at most approximately 6,000 tpm or at most approximately 5,000 from the perspective of concealment of the non-engaging surface of the female material of the obtained touch fastener.

Both S-twisted yarn (that is, yarn twisted in an S-direction) and Z-twisted yarn (that is, yarn twisted in a Z-direction) can be used as finished yarn. It is preferable to use S-twisted yarn and Z-twisted yarn in combination from the perspective of preventing the curling of the knitted fabric. The advantages of curl prevention are marked in the production process of an absorbent article using the touch fastener female material. Specifically, curl prevention contributes to enhanced efficiency of the conveyance of the touch fastener female material by the suction roll described above. In a preferred embodiment, the back yarn has an alternating arrangement of one or a plurality of S-twisted yarns and one or a plurality of Z-twisted yarns in the well direction. For example, S-twisted yarns and Z-twisted yarns may be arranged alternately for each yarn in the well direction, as in SZSZSZ, and S-twisted yarns and Z-twisted yarns may also be arranged alternately in units of a plurality of yarns in the well direction, as in SSZZSSZZSSZZ. In a preferred embodiment, S-twisted yarns and Z-twisted yarns are arranged alternately for each yarn (that is, as in SZSZSZ) in the well direction as a back yarn from the perspective of curl prevention.

The finished yarn may have elasticity. Elasticity may be provided by the elasticity of the material constituting the yarn, by the manner of twisting of the yarn, or a combination thereof.

In several embodiments, the back yarn may further include elastic yarn having the same fineness as the finished yarn or a smaller fineness than the finished yarn. The elastic yarn is not meant to be finished yarn. An example of elastic yarn is a polyurethane elastic yarn. In an exemplary embodiment, the back yarn has an alternating arrangement of one or a plurality of finished yarns and one or a plurality of elastic yarns in the well direction. For example, a plurality of finished yarns and one elastic yarn may be arranged alternately. In a preferred embodiment, the fineness (total fineness) of the elastic yarn is at least ⅓ and at most 1 times the fineness of the finished yarn. For example, when the fineness of the finished yarn is 84 dtex is, the fineness of the elastic yarn may be at least approximately 28 dtex and may be at most approximately 84 dtex.

The front yarn and middle yarn may be finished yarn or unfinished yarn (that is, original yarn that has not been processed).

The female material of the present disclosure may also have a printed part and additional elements as necessary in addition to the knitted fabric. In a preferred embodiment, a printed part is formed by coating on the knitted fabric. Since the non-engaging surface of the knitted fabric of the present disclosure has excellent smoothness and concealment, a printed part with a good external appearance can be formed even when the printed part is disposed directly on the knitted fabric. In particular, the good concealment of the non-engaging surface is advantageous for the formation of the printed part by coating.

Examples of additional elements include components which impart adhesiveness by adhesive processing, components which impart strength by resin processing, knitted fabrics, woven fabrics, nonwoven fabrics, paper, or laminates thereof, and the like. The method of lamination is not particularly limited, but a conventionally known method such as coating, dry lamination, extrusion lamination, wet lamination, thermal lamination, or ultrasonic waves, or the like can be used.

The printed part 30 can be fixed directly onto the knitted fabric 20. The statement that "the printed part is fixed directly onto the knitted fabric" means that the printed part is disposed on the knitted fabric without using another member or layer (that is, in contact with the knitted fabric), and the printed layer is essentially unremovable from the knitted fabric while maintaining its form. That is, as described above, the printed part 30 can be provided on the non-engaging surface of the base structure 24 of the knitted fabric 20. In addition, a part of the printed part 30 may also be present between each of the yarns (back yarn and middle yarn) constituting the base structure 24 of the knitted fabric 20. In this way, the form of the printed part is maintained by the knitted fabric, and the printed part is supported on the knitted fabric as a support. Typically, the printed part is not fixed to a substrate layer such as a printed layer support film or another member in the female material and is present in a state fixed to only the knitted fabric. Accordingly, a female material formed by laminating a knitted fabric with a printed sheet having a printed layer support film and an ink layer provided thereon is distinguished from the female material of the present disclosure in that the printed layer can ordinarily be peeled from the base material layer together with the printed layer support film.

The printed part may consist of only ink or may have a base coat and/or a top coat in addition to ink. The ink and optional base coat and top coat may respectively be present as a continuous layer on the knitted fabric or may be disposed non-continuously, and an appropriate design can be formed in accordance with the desired purpose or the intended pattern of the ink. The design may be selected appropriately in the form of characters, a picture, a pattern, or the like.

Various conventionally known inks may be used as the ink material, and water-based and solvent-based inks are used. A resin ordinarily used conventionally can be used as the resin contained in the ink. Examples include acrylic resins, polyurethane resins, polyamide resins, urea resins, polyester resins, vinyl chloride resins, epoxy resins, polyvinyl alcohol resins, ethylene-vinyl acetate copolymer resins, olefin resins, epoxy resins, petroleum resins, cellulose derivative resins, and natural resins such as rosin derivatives, and the like. With an ink having excellent solidity, the ink is unlikely to come off, even if the ink is exposed at the time of the use of an article having the female material of the present disclosure. From this perspective, urethane inks, epoxy inks, and the like, for example, are suitable. In addition, the ink itself may also be a hot melt type adhesive.

In a typical embodiment, the printed part can be formed by coating on the non-engaging surface of the knitted fabric. Coating can be performed with a conventionally known method used for printing by coating. The fact that the printed part is formed by coating is advantageous in that decreases in air permeability and flexibility, which may arise in a female material having a printed layer support film, for example, can be avoided. In several embodiments, the female material of the present disclosure further having a printed part formed by coating may also have good air permeability, flexibility, and extensibility. Such merits are advantageous for the feeling when worn when the female material is used in an absorbent article such as a sanitary product, for example.

The female material of the present disclosure can eliminate the use of materials that invite increases in cost (for example, a printed layer support film, an adhesive, or the like), so the material can be produced with a simple configuration and production method, which is advantageous from the perspectives of raw material cost and production cost.

In a preferred embodiment, the female material may have a basis weight of from approximately 10 to approximately 100 g per 1 square meter. When the basis weight is at least approximately 10 g/m2, the form of the female material can be maintained easily. When the basis weight is at most approximately 100 g/m2, the rigidity of the female material is not too large, and the flexibility of the female material is good.

In a preferred embodiment, the female material is flexible and pliable. For example, the rigidity of the female material is preferably at least approximately 0.8 N/inch and at most approximately 3.5 N/inch in the MD direction (middle yarn direction) and at least approximately 0.3 N/inch and at most approximately 3.5 N/inch in the CD direction (back yarn direction) forming an angle of 90° with the MD direction. When the rigidity is within the ranges described above, the female material may have excellent flexibility while maintaining good mechanical strength.

In a preferred embodiment, the female material has excellent air permeability. More specifically, the air permeability of the female material measured by the Gurley method is preferably at most approximately 5 sec/100 cc from the perspective that a sanitary product can be provided with a good fit when worn. The air permeability is more preferably at most approximately 3 sec/100 cc and even more preferably at most approximately 1 sec/100 cc. The lower limit is not particularly limited but is at least approximately 0.1 sec/100 cc in certain embodiments.

Additional processing such as raising, embossing, dying, and coloring may be further applied as appropriate to the touch fastener female material 10. In addition, the knitted fabric 20 may be fully or partially dyed. In particular, when used as a member of an absorbent article such as a diaper, the gloss such as the luster or gleam can be eliminated, which makes it possible to achieve an excellent aesthetic appearance.

Another embodiment of the present disclosure provides a touch fastener including the touch fastener female material described above and a touch fastener male material (also simply called a "male material" in the present disclosure).

Figure 5:
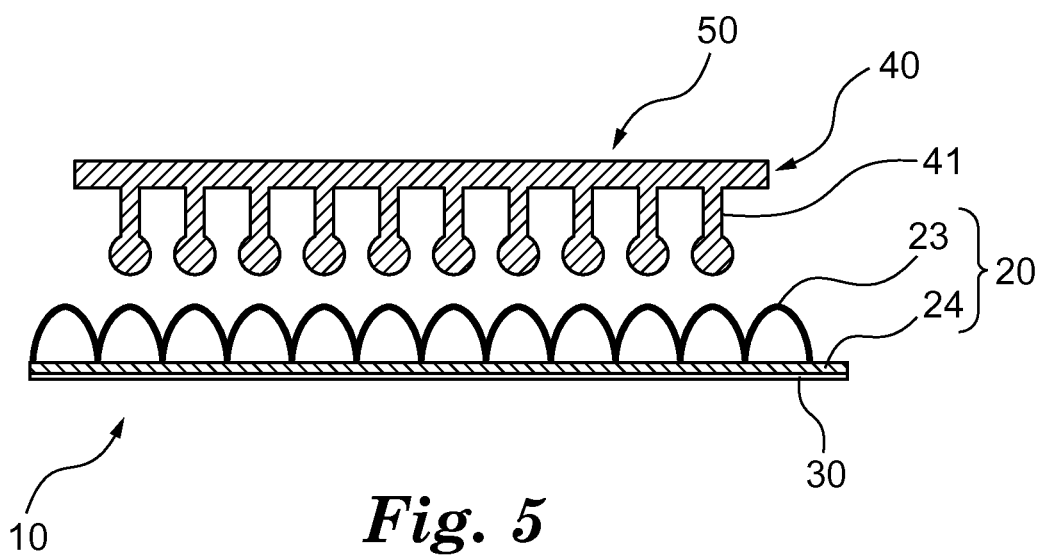
FIG. 5 is a schematic diagram illustrating the cross-sectional structure of the touch fastener of an embodiment of the present disclosure.

FIG. 5 is a schematic diagram illustrating the cross-sectional structure of the touch fastener of an embodiment of the present disclosure. Referring to FIG. 5, a male material 40 ordinarily has a sheet-like base 50 and a plurality of hook engaging elements 41 disposed as protrusions on the base. The shape of the hook engaging elements is not particularly limited, but a columnar form such as a cylinder, a square prism, a hexagonal prism, or the like may be used, and the shape may have a top part such as a disc type, mushroom type, key type, wedge type, or arrowhead type top part, for example, in order to enhance the mechanical engaging effect. This is because such a top part can be mechanically engaged with the opposing engaging surface more favorably, and the attachment/detachment operation can also be performed easily.

For example, the density of the hook engaging elements in the male material is typically from approximately 500 to approximately 5,000 elements per 1 square inch, and in certain embodiments, a material having a density of 1,600 elements per 1 square inch is used.

Various thermoplastic resin materials may be used as the material of the engaging elements in the male material, examples of which include polyethylenes (for example, high-density polyethylene), polypropylene, polystyrene, polyvinyl chloride, polyethylene terephthalate, polybutylene terephthalate, nylon, polycarbonate, polymethyl methacrylate, polyacetal, polymethyl pentene, acrylonitrile-styrene-butadiene, polyphenylene ether, polyphenylene sulfide, styrene elastomers such as styrene-butadiene-styrene and styrene-isoprene-styrene, olefin elastomers such as ethylene-α-olefin copolymers, ester elastomers, amide elastomers, urethane elastomers, vinyl chloride elastomers, silicone elastomers, fluorine elastomers, and alloys thereof. An example of a male material is hook tape (CS-600) sold by 3M Japan (Ltd.).

The touch fastener of the present disclosure can be used to fix various articles such as various components in clothing, automotive interior materials, or the like, for example. However, since the touch fastener of the present disclosure has good air permeability, flexibility, and extensibility originating from its configuration, it is particularly suitable as a touch fastener for an absorbent article (for example, a sanitary product such as a disposable diaper).

In several embodiments, when the touch fastener is used in an absorbent article and in a disposable diaper, in particular, it is preferable to take into consideration the engaging properties between the female material and the male material and the performance of the female material, in particular. In an ordinary disposable diaper, a pair of left and right male materials are provided on both sides of the back side of the wearer, and a pair of left and right female materials are provided on the front abdominal area. Accordingly, the male and female materials are respectively engaged at two locations on the left and right sides of the disposable diaper, but it is preferable for the difference in engaging force on the left and right in this case—that is, the difference between the peeling force in the left direction and the peeling force in the right direction—to be small from the perspective of the reliable fastening of the disposable diaper using the touch fastener.

For example, a female material with a structure in which the front yarns project alternately on the left and right with respect to the middle yarns is preferable in that the difference in engaging force with the male material on the left and right is small.

Examples of absorbent articles include diapers for children, adults, and pets and napkins for sanitary use and other applications, and the like. In a typical embodiment, the sanitary product is a diaper. The good smoothness and concealment in the knitted fabric of the present disclosure are also advantageous for stable conveyance of the diaper and by the suction hole provided in the suction roll of an assembly line.

In a preferred embodiment, the absorbent article has excellent air permeability. More specifically, the air permeability of the absorbent article measured by the Gurley method is preferably at most approximately 5 sec/100 cc from the perspective that the absorbent article can be provided with a good fit when worn. The air permeability is more preferably at most approximately 3 sec/100 cc and even more preferably at most approximately 1 sec/100 cc. The lower limit is not particularly limited but is at least approximately 0.1 sec/100 cc in certain embodiments.

The production method of the absorbent article is not particularly limited, but the following method may be given as an example. Any conventionally known elements can be used as elements other than the touch fastener of the absorbent article, and detailed descriptions thereof will not be given here. In the absorbent article, any known method can be used as the method for attaching the touch fastener to the application part. One surface of the touch fastener (for example, the surface on which the printed part is formed on the female material) is joined to the application part by a conventionally known junction method (adhesion by glue, heat sealing, or ultrasonic processing, sewing, mechanical fastening with a stapler, or the like). In fastening with glue, a known adhesive such as a synthetic rubber adhesive such as SIS or SBS, an olefin adhesive, an acrylic adhesive, a silicone adhesive, or an EVA adhesive is selected appropriately as necessary, but the present disclosure is not limited to these resins.

EXAMPLES

Exemplary embodiments of the present invention will be described in further detail hereinafter using examples, but the present invention is not limited to these examples.
<Evaluation Methods>
1. Light Transmittance The light transmittance of the knitted fabric was measured in accordance with a total light transmittance test method (JIS K7361). NDH200 manufactured by Nippon Denshoku Industries Co., Ltd. was used as a measurement device. A 50 mm×50 mm test piece cut out from the knitted fabric was fixed to a sample holder of the measurement device. The test piece was irradiated with white light approximately 1 cm in diameter, and the total light transmittance was measured.
2. Lab Color Space L*

The Lab color space L* of the knitted fabric was measured using a spectrophotometer (CM-2600d manufactured by Konika Minolta, Inc.). A 50 mm×50 mm test piece cut out from the knitted fabric was placed on a black plate. Next, a measurement instrument was placed on the test piece, and the sample was fixed. After the test piece was irradiated with light 8 mm in diameter (light source: xenon lamp), L*a*b* was measured, and L* was read out.

3. Thickness

The thickness of the knitted fabric was measured using a thickness gauge (No. 2109FL manufactured by Mitutoyo Co., Ltd.). A 100 mm×100 mm test piece cut out from the knitted fabric was sandwiched between the gauge probes of the thickness gauge, and the thickness was measured. The measurement probes were semispherical in shape.

4. 20% Stretch Load

A test piece of 50 mm in the CD direction and approximately 25 mm in the MD direction cut out from the knitted fabric was fixed between the chucks of a Tensilon tension tester (RTC-1225 manufactured by Orientec Co., Ltd.), and the test piece was extended in the lengthwise direction at a rate of 300 mm/min. The extension distance in the extension process and the tensile load corresponding to the extension distance were plotted, and a relational curve of the extension distance and the tensile load (horizontal axis: extension distance (mm), vertical axis: tensile load (N)) was obtained. The value of the tensile load when the extension distance was 5 mm (that is, an extension rate of 20%) was read out from the obtained relational curve.

5. Engaging Force

The engaging force was measured with the following procedure. A female material test piece 100 mm long and 50 mm wide was placed on a 90° shear jig so that the non-engaging surface corresponded to the jig. A male material 20 mm long and 25 mm wide having a hook (3M mechanical fastener hook NC-2050, available from 3M Japan (Ltd.)) placed gently on the female material test piece so that the hook surface opposed the female material test piece. In the 90° shear jig, the surface with which the male material makes contact is made to be smooth. A 2.0 kg hand roller was slowly rolled over the male material one time in the width direction at approximately 300 mm/min. Next, a clip was attached to the end part of a paper leader of the male material. After a 1 kg weight was suspended for 2 seconds from the clip, the weight and the clip were removed.

Next, the female material test piece was placed in the 90° shear jig, and the paper end part of the male material was inserted into the upper side port of a tensile tester. The hook end part of the male material was placed directly beneath the upper side port. A peeling test was performed while pressing downward so that the female material test piece did not move, and the engaging force was measured.

6. External Appearance of the Non-Engaging Surface

The external appearance of the non-engaging surface of the knitted fabric was photographed with a microscope (VHX-1000 manufactured by Keyence Corporation) for Example 2 and Comparative Example 3.

<Production of Female Material>

Examples 1 to 4 and Comparative Examples 1 to 3

A touch fastener female material was produced with the following procedure.
Knitting machine: 28-gauge, three-bar, single-tricot knitting machine (manufactured by Karl Mayer)
Yarn arrangement: one-in-one-out
Yarn Types:

Front yarn (fed from front bar): 84T/36 (decitex/filament, same hereafter), unfinished yarn (polyester original yarn) (commercially available from Teijin Ltd.)

Middle yarn (fed from middle bar): 22T/1, unfinished yarn (polyester original yarn) (commercially available from Toray Ltd.)

Back yarn (fed from back bar)

Examples 1 to 4 and Comparative Examples 1 and 2

84T/36, finished yarn (polyester false-twist finished yarn) (false twist conditions: 4,000 tpm (twist per meter), available from Yamagoe Ltd.)

Comparative Example 3

84T/36, unfinished yarn (polyester original yarn) (commercially available from Teijin Ltd.)
Knit Structure and Runner:

Front yarn: 1-0/5-6/10-11/6-5 (see FIGS. 3A and 3B), 176 cm/480 courses

Middle yarn: 1-0/0-1/0-1/1-0 (see FIGS. 3A and 3B), 130 cm/480 courses

Back yarn: as described in Table 1

Comparative Example 4

A commercially available nonwoven fabric loop with a basis weight of 43 g/m2 (nonwoven fabric loop made of fibers configured from polypropylene and polyethylene, produced by carding-based web production and then embossed patterning and binding between fibers) was used.

The results are shown in Table 1.

TABLE 1

|  | Example 1 | Example 2 | Example 3 | Example 4 | Comparative Example 1 |
|---|---|---|---|---|---|
| Fabric type | Knitted fabric | Knitted fabric | Knitted fabric | Knitted fabric | Knitted fabric |
| Back yarn type | Finished yarn | Finished yarn | Finished yarn | Finished yarn | Finished yarn |
| Back yarn stitch | Lap | Lap | Lap | Lap | Seam |
| Back yarn knit structure | 0-0/5-5 | 0-0/7-7 | 0-0/9-9 | 0-0/3-3 | 1-0/4-5 |
| Back yarn manner (cm/480 courses) | 120 | 208 | 290 | 390 | 390 |
| Courses | 22 | 22 | 22 | 22 | 22 |
| Basis weight actual measurement (g/m$^2$) | 38 | 46 | 55 | 33 | 55 |
| Light transmittance (%) | 73.3 | 67.8 | 63.7 | 77.1 | 66.0 |
| Lab color space L* 1) | 62.9 | 69.5 | 68.0 | 58.2 | 69.7 |
| Thickness (μm) |  |  |  |  |  |
| Between back yarn knots (A) | 33.6 | 36.8 | 45.0 | 10.8 | 41.8 |
| Between back yarn and middle yarn knots (B) | 87.6 | 103.2 | 109.0 | 80.6 | 146.6 |
| Difference (B)-(A) | 54.0 | 66.4 | 64.0 | 69.8 | 104.8 |
| 20% Stretch load (N/25 mm) 2) | 0.43 | 1.32 | 3.38 | — | — |

TABLE 1-continued

| Engaging force (N/25 mm) | | 5.1 | 4.7 | 5.5 | 5.4 | 3.3 |
|---|---|---|---|---|---|---|
| | | | | Comparative Example 2 | Comparative Example 3 | Comparative Example 4 |
| | Fabric type | | | Knitted fabric | Knitted fabric | Nonwoven fabric |
| | Back yarn type | | | Finished yarn | Unfinished yarn | |
| | Back yarn stitch | | | Seam | Lap | — |
| | Back yarn knit structure | | | 1-0/4-5 | 0-0/7-7 | — |
| | Back yarn manner (cm/480 courses) | | | 530 | 208 | — |
| | Courses | | | 15 | 22 | — |
| | Basis weight actual measurement (g/m$^2$) | | | 43 | 44 | 43 |
| | Light transmittance (%) | | | 76.5 | 75.1 | — |
| | Lab color space L* 1) | | | 58.7 | 63.1 | — |
| | Thickness (μm) | | | | | |
| | Between back yarn knots (A) | | | 36.4 | 29.6 | — |
| | Between back yarn and middle yarn knots (B) | | | 101.6 | 94.8 | — |
| | Difference (B)-(A) | | | 73.2 | 65.2 | — |
| | 20% Stretch load (N/25 mm) 2) | | | — | — | 10.36 |
| | Engaging force (N/25 mm) | | | 3.8 | 2.4 | 2.0 |

1) Black used for background
2) Stretched in CD horizontal direction

The touch fastener female materials of the examples yielded a small difference in thickness (B)-(A) and had good smoothness while having a low light transmittance and good concealment due to the types and arrangements of the back yarns. Of these, in Examples 1 to 3 in which N in the back yarn knit structure 0-0/N-N was 5, 7 and 9, the concealment and smoothness were even better than in Example 4, which had an N of 4. In addition, in a comparison with the nonwoven fabric loop of Comparative Example 4, it was confirmed that the touch fastener female materials of the examples demonstrated a superior engaging force and extensibility. On the other hand, in Comparative Examples 1 and 2 in which the back yarns formed seams, the smoothness was inferior to that of the examples.

Figure 6A:
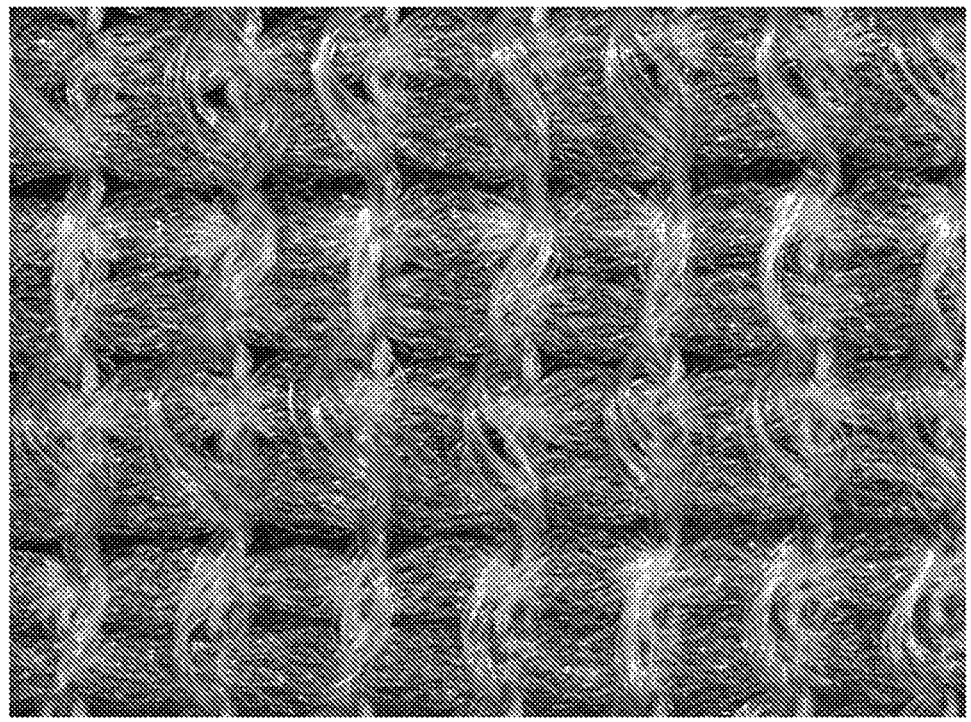
FIG. 6 illustrates the external appearance of the non-engagement surfaces of the knitted fabrics in an Example 2 ((a) in the drawing) and a Comparative Example 3 ((b) in the drawing).
Figure 6B:
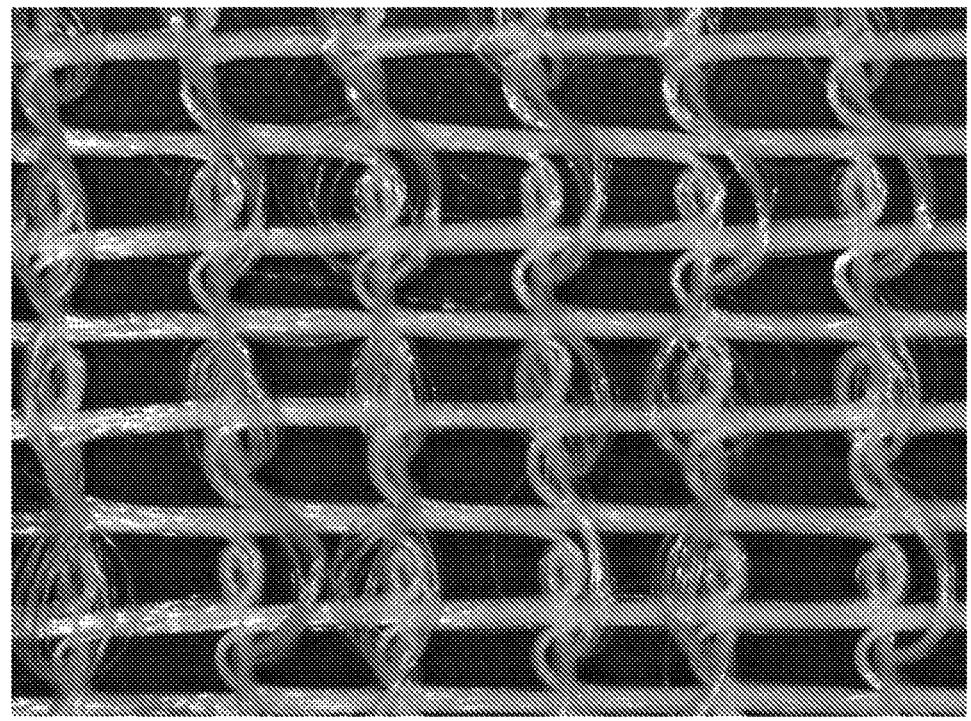

In addition, in Comparative Example 3 in which the back yarn was not a finished yarn, the engaging force was smaller than that of the examples. Further, the external appearance of the non-engaging surface of Comparative Example 3 was compared with that of Example 2 having the same back yarn knit structure (here, the knitted fabric of Comparative Example 3 was produced in the same manner as in Example 2 with the exception that the back yarn was an unfinished yarn). FIG. 6 illustrates the external appearance of the non-engagement surfaces of the knitted fabrics in Example 2 ((a) in the drawing) and Comparative Example 3 ((b) in the drawing). The field of view in both drawings is 10 mm (vertical)×15 mm (horizontal). In Example 2 in which the back yarn was a finished yarn, the non-engaging surface had an appearance with fine seams (good concealment), whereas in Comparative Example 3 in which the back yarn was an unfinished yarn, the non-engaging surface had an appearance with many gaps (poor concealment).

Next, in order to confirm the printing aptitude of the touch fastener female material samples of Examples 1 to 4 and Comparative Examples 1 to 3, the Japanese character for "correct" was printed on the non-engaging surface side of each sample, and the clarity of the character after printing was observed visually. In all of the samples of the examples, the character "correct" was clear, and an even clearer printed appearance was achieved in the samples of Examples 1 to 3 in which N of the back yarn knit structure was large (large amplitude). On the other hand, in the samples of Comparative Examples 1 and 2, the contour of the character "correct" was blurry, and a poor appearance was observed.

This may be due to the fact that the back yarns formed seams and the smoothness of the non-engaging surface became poor due to the seams in Comparative Examples 1 and 2. In addition, since the sample of Comparative Example 3 had many gaps, it was not possible to print the character "correct" on the non-engaging surface. The ink used for printing escaped to the sample engaging surface (back surface) side through the gaps and soaked into the mount on which the sample was mounted.

The touch fastener female material and touch fastener of the present disclosure can be suitably applied to absorbent articles such as sanitary materials including diapers for children, adults, and pets and napkins for sanitary use and other applications, for example.

REFERENCE SYMBOLS

10 touch fastener female material
20 knitted fabric
21, 21A back yarns
22, 22A, 22B, 22C middle yarns
22a, 22c, 23b, 23d laps
22b, 22d, 23a, 23c seams
23, 23A front yarns
24 base structure
30 printed part
40 male material
41 engaging element
50 base
T1, T2, T3, T4 end parts

What is claimed is:

1. A touch fastener female material comprising a knitted fabric;
   the knitted fabric including back yarns, middle yarns, and front yarns;
   at least 50% of the back yarns being finished yarns; and
   the back yarns being arranged in accordance with a 0-0/N-N (where N is an odd number) knit structure,
   wherein the middle yarns form seams and laps alternately;
   each of the back yarns is alternately connected to two of the middle yarns at each end part on the 0-0 side and the N-N side; and
   wherein the back yarn is connected to the seam of one of the two middle yarns at one end part on the 0-0 side or the N-N side and is connected to the lap of the other of the two middle yarns at the other end part on the O-O side or the N-N side, wherein the back yarns have an alternating arrangement of one or a plurality of S-twisted yarns and one or a plurality of Z-twisted yarns in a wale direction.

2. The touch fastener female material according to claim 1, wherein N is 5, 7, or 9.

3. The touch fastener female material according to claim 1, wherein the middle yarns alternately form seams and laps; the front yarns have at least laps arranged at the positions of the seams of the middle yarns; and the front yarns alternately project to the left and right with respect to the middle yarns.

4. The touch fastener female material according to claim 3, wherein the back yarn further includes an elastic yarn having the same fineness as the finished yarn or a smaller fineness than the finished yarn.

5. The touch fastener female material according to claim 4 further having a printed part.

6. A touch fastener comprising the touch fastener female material according to claim 1 and a touch fastener male material.

7. An absorbent article comprising the touch fastener according to claim 6.

* * * * *